United States Patent [19]

Start

[11] 4,395,548

[45] Jul. 26, 1983

[54] PROCESS FOR PRODUCTION OF AN ALKALI METAL DICHLOROISOCYANURATE AND TRICHLOROISOCYANURIC ACID

[75] Inventor: John F. Start, Trenton, N.J.

[73] Assignee: FMC Corporation, Philadelphia, Pa.

[21] Appl. No.: 365,060

[22] Filed: Apr. 2, 1982

[51] Int. Cl.$^3$ ............................................ C07D 251/36
[52] U.S. Cl. .................................................... 544/190
[58] Field of Search ......................................... 544/190

[56] References Cited

U.S. PATENT DOCUMENTS

| | | | |
|---|---|---|---|
| 2,913,460 | 11/1959 | Brown et al. | 260/248 |
| 2,938,032 | 5/1960 | Hugel et al. | 260/248 |
| 2,969,360 | 1/1961 | Westfall | 260/248 |
| 2,975,178 | 3/1961 | Hugel et al. | 260/248 |
| 3,073,823 | 1/1963 | Merkel et al. | 260/248 |
| 3,120,522 | 2/1964 | Olson et al. | 260/248 |
| 3,178,429 | 4/1965 | Vazopolos | 260/248 |
| 3,336,228 | 8/1967 | Fuchs et al. | 252/99 |
| 3,415,823 | 12/1968 | Moore et al. | 260/248 |
| 3,453,274 | 7/1969 | Murrin et al. | 260/248 |
| 3,474,096 | 10/1969 | Kagawa | 260/248 |
| 3,534,033 | 10/1970 | Kagawa et al. | 260/248 |
| 3,757,018 | 9/1973 | Mesiah | 260/248 C |
| 3,803,144 | 4/1974 | Berkowitz | 260/248 C |
| 3,810,892 | 5/1974 | Mesiah et al. | 260/248 C |
| 3,919,217 | 11/1975 | Sawhill | 260/248 C |

OTHER PUBLICATIONS

Chapin, Robert M., The Effect of Hydrogen-ion Concentration on the Decomposition of Hypohalites, Jacs, 56, 2211-2215 (1934).

*Primary Examiner*—John M. Ford
*Attorney, Agent, or Firm*—Richard E. Elden; Eugene G. Horsky

[57] ABSTRACT

A process to manufacture trichloroisocyanuric acid of commercially acceptable size and quality from a mother liquor used to produce an alkali metal salt of dichloroisocyanurate by monitoring and, if necessary, adjusting the mol ratio of available alkalinity to chlorine required to convert all of the triazine compounds in the mother liquor to trichloroisocyanuric acid to be between 1.0 and 1.3 with an alkali metal salt of carbonic acid.

15 Claims, No Drawings

PROCESS FOR PRODUCTION OF AN ALKALI METAL DICHLOROISOCYANURATE AND TRICHLOROISOCYANURIC ACID

This invention is an improved process in which trialkali metal cyanurate is chlorinated in two steps to form an alkali metal dichloroisocyanurate and trichloroisocyanuric acid.

The chlorinated cyanuric acids and their salts are important commercial products as they are useful bleaching and sanitizing agents. The most important commercial cyanurates are the trichloroisocyanuric acid (TCCA) and the monosodium dichloroisocyanurate (NaDCC) salts.

Mesiah et al, U.S. Pat. No. 3,810,892, teach that the same production equipment is commonly employed for the alternate production of both dichloroisocyanuric acid (DCCA), which is converted to the sodium or potassium salt, and TCCA. Mesiah et al also teach that alternating between production of both DCCA and TCCA requires process turn arounds; Mesiah et al indicate the desirability for a single process which could produce both NaDCC and TCCA simultaneously. However, the process employed by Mesiah et al still requires the intermediate production of DCCA and a separate step to produce the sodium or potassium salt. The intermediate production of DCCA requires additional production steps and manpower, thus increasing operating costs. Therefore, it would be an advantage for a process to produce both NaDCC and TCCA without isolating an intermediate product DCCA.

It is well-known that the trisodium cyanurate salt can be chlorinated with 2 mols of chlorine to form NaDCC or with 3 mols of chlorine to form TCCA. It has often been pointed out in the prior art that while this is practical in the laboratory, it is difficult or impossible in a large-scale commercial plant. For example, in U.S. Pat. No. 2,969,360, Westfall teaches that yields decrease and underchlorinated products are obtained as batch sizes increase or attempts are made to run the process continuously. Westfall further states that the problems can be reduced by increasing the total amount of alkali used above that theoretically required and by increasing the amount of chlorine.

For commercial plants Westfall suggests the two-stage chlorination process. In the first stage, one-half of the chlorine is added while the reactants are maintained at an alkaline pH. In the second stage, the second half of the chlorine is added at a pH of 1.5 to 3.5. The products obtained are DCCA if the feed is disodium cyanurate or TCCA if the feed is trisodium cyanurate; the alkali metal salts are produced by neutralizing the DCCA with a suitable base. The process of Westfall, with modifications to adjust the pH ranges of the first and second stages, has been adopted throughout the industry for production of chlorinated cyanurates.

The problem minimized by the two-stage process of Westfall is the formation of very small crystals of the chlorinated cyanuric acid. However, very fine crystals still form frequently and the reaction mixture is then impossible to filter or centrifuge on a commercial scale.

In U.S. Pat. No. 3,120,522, Olson et al recognize this fines problem and teach the use of a mixture of chlorinated hydrocarbons to assist in the formation of large crystals of chlorinated cyanuric acid. Similarly, in U.S. Pat. No. 3,453,274, Murrin et al teach the localized addition of an alkali metal hydroxide to adjust the pH in the second stage chlorinator, together with the use of surfactant to encourage the growth of large cyanuric acid crystals. This localized addition of an alkali metal hydroxide taught by Murrin et al can cause decomposition of the triazine ring to form explosive nitrogen trichloride.

Kagawa et al in U.S. Pat. No. 3,534,033 teach that nitrogen trichloride formation may be minimized by chlorinating in a first stage to more than pH 9 and in a second stage to less than pH 4. Kagawa et al are not concerned with the triazine ring destruction which takes place in the range of pH 9 to pH 11, but only in nitrogen trichloride formation. However, Kagawa et al teach that the maximum nitrogen trichloride formation takes place in the range of pH 5 to pH 7, and must be avoided.

The teaching of Kagawa et al confirms the earlier work of Chapin in the *Journal of the American Chemical Society*, 56, pp 2211–15 Nov. (1934) concerning the instability of hypochlorous acid in the same range of pH 5 to pH 7. Chapin specifically teaches that acetate, borate, and carbonate accelerate the decomposition of hypochlorous acid.

Merkel et al teach, in U.S. Pat. No. 3,073,823, that explosive chlorine compounds form in the the production of DCCA and TCCA by the chlorination of disodium cyanurate and trisodium cyanurate respectively. Merkel et al teach that these explosive compounds may be destroyed by adding an excess of sodium carbonate or sodium bicarbonate to the slurry of DCCA or TCCA and chlorinating further. The process of Merkel et al does not avoid the formation of these explosive compounds and requires the uneconomic use of an excess of chlorine and alkali. Further, the process of Merkel et al is not adaptable to a process to produce NaDCC by chlorinating trisodium cyanurate; it is capable of producing only fine crystals of TCCA, which cannot be processed in commercial equipment.

The present invention provides a process to make both an alkali metal dichloroisocyanurate and trichlorisocyanuric acid by chlorinating at 10° C. to 30° C. an alkali metal salt of cyanuric acid, such as trisodium cyanurate in a first chlorinator at pH 5 to 9, preferably at pH 6.5 to 7.5, thus forming a slurry of the alkali metal salt of dichloroisocyanuric acid in a mother liquor. The alkali metal salt of dichloroisocyanuric acid is separated from the mother liquor and dried by conventional means. The mother liquor is then monitored for pH. If the pH of the mother liquor feed to the second chlorinator is equal to the pH of the slurry when discharged from the first chlorinator, the mol ratio is still equal to 1. Mol ratio as used herein is equal to the mols of available alkalinity in a solution or slurry of the dichloroisocyanurate divided by the mols of chlorine required to convert all of the triazine compounds in the solution or slurry to trichloroisocyanuric acid. If the pH of the solution or slurry feed to the second chlorinator drops, the loss of available chlorine is determined. A sufficient quantity of an alkali metal salt of carbonic acid is then added to adjust the mol ratio to be within the range of 1.0 to 1.3, preferably to be within the range of 1.0 to 1.15.

The mother liquor is then added to the second continuous chlorinator which is held at a temperature of 10° C. to 30° C., preferably 10° C. to 20° C. The pH of the second chlorinator is maintained at 2.5 to 3.5, preferably at 3.3 to 3.0. The slurry from the chlorinator is then separated in a conventional filter or centrifuge and the solid TCCA is dried by conventional means. The effluent may be discarded or recycled to the first chlorinator.

The present invention recognizes there are three important factors for a commercial crystallization process: (1) the raw material yield, (2) the assay of the product, and (3) a satisfactory crystal size and shape. The crystal size and shape is important as the crystal slurry must be capable of being rapidly dewatered using commercial equipment. TCCA forms prismatic crystals and for ease of dewatering a short, broad prism is preferred over a long, narrow prism.

These three factors stated above are critical for economic commercial production of TCCA. The turbidity of the mother liquor after separation is another indication of the presence of small crystals. It has unexpectedly been found that the inability to form sufficient hypochlorous acid to fully chlorinate the available dichloroisocyanurate to TCCA (a mol ratio of less than one) adversely affects each of these three factors. This low mol ratio can be caused by the decomposition of hypochlorous acid to form hydrochloric acid according to the following reactions:

$$2HOCl \rightarrow 2HCl + O_2$$

$$3HOCl \rightarrow HClO_3 + 2HCl,$$

or by a reaction consuming hypochlorous acid, such as the formation of chloroamine:

$$HOCl + NH_3 \rightarrow NH_2Cl + H_2O,$$

or by the consumption of available alkalinity as in the destruction of a triazine ring:

$$2C_3H_3O_3N_3 + 9Cl_2 + 18NaOH \rightarrow 6CO_2 + 3N_2 + 18NaCl + 12H_2O$$

It has been observed that the pH of a solution of NaDCC drops gradually on standing and readjustment of the pH with an alkali metal hydroxide rarely results in a satisfactory TCCA product. The addition of an alkali metal hydroxide equivalent to the decrease of the available chlorine, usually results in a high pH, frequently above pH 9, and further decomposition takes place. However, it has been found that the addition of an alkali metal salt of carbonic acid, such as sodium bicarbonate will provide the necessary total alkalinity to adjust the mol ratio to at least unity without increasing the pH above 9. Furthermore, the TCCA produced from the adjusted solution generally is satisfactory according to the three factors supra.

EXPERIMENT 1

This experiment illustrates the first step in the process, the chlorination to sodium dichloroisocyanurate. Further, the experiment illustrates the inability to rely on pH alone to adjust the mol ratio of the mother liquor prior to the second chlorination to TCCA.

1A. Two liters of an 8% slurry of cyanuric acid (160 g) and 295 g of a 50% NaOH solution were fed to a continuous laboratory chlorinator at 30° C., together with 176 g Cl$_2$ at a rate to maintain the slurry at pH 7. A yield of 243 g of NaDCC was recovered and dried as the dihydrate.

On storage at 25° C. for 48 hours, the available chlorine in the 1.888 liters of filtrate fell from 48.10 g/l to 45.48 g/l, while the pH dropped from 6.90 to 5.60. A loss of 1.48 g/l of available chlorine was observed which was caused by the decomposition of hypochlorous acid to oxygen plus hydrochloric acid. However, adjusting the pH of one liter of solution to pH 6.9 required only 0.67 g NaOH; the addition of the 1.48 g NaOH equivalent to the 1.48 g/l decrease of available chlorine resulted in a pH of 8.98. On chlorination, a 94.6% yield was obtained of the remaining cyanuric acid values as TCCA with an available chlorine of 85.1% (97.9% of theory). The experiment indicated that pH alone cannot be used to determine whether sufficient sodium hydroxide is present to result in full chlorination of the solution to TCCA.

1B. The balance of the filtrate, 0.888 liter, was treated with 1.82 g NaOH, an excess sufficient to compensate for the low assay of Experiment 1A. As this resulted in a pH of 9.8, the solution was sparged with chlorine to drop the pH to 8.9 before chlorination in the continuous chlorinator to pH 2.8 as above.

A 90.9% yield of fine crystals of TCCA was obtained with an assay of 84.5% available chlorine (92.2% of theory). The yield and assay were not improved over Experiment 1A; the short exposure to pH 9.8 was sufficient for side reactions to prevent the growth of crystals of a satisfactory size.

EXPERIMENT 2

Experiment 2 was designed to establish conditions for a subsequent screening program by selecting marginal conditions for continuous production of TCCA by chlorination of a mother liquor containing NaDCC so that either favorable or adverse effects could be observed.

A 4 liter solution containing 240 g of NaDCC dihydrate was chlorinated in a continuous laboratory chlorinator at 10° C. The average holding time of the chlorinator was 38 minutes; the results are shown in Table I. A surfactant, sodium dodecylbenzenesulfonate, was used in Runs 2–14 as taught by U.S. Pat. No. 3,453,274 and found beneficial. Sodium chloride was found to have an adverse effect on the crystal formation. An increase in the degree of chlorination as indicated by the final pH was found to increase the yield and the size of the TCCA crystals. The solution represented by Run 14 had satisfactory crystal properties yet was capable of responding to favorable, as well as adverse effects of additives and was, therefore, suitable for the control in subsequent experiments.

EXPERIMENT 3

The process of Experiment 2 was repeated using the following conditions unless otherwise noted and the results are reported in Table II.

4 liters of feed solution
51.6 g/l NaDCC
90 g/l NaCl
50 mg/l sodium dodecylbenzenesulfonate
feed pH 6.6
chlorination to pH 3.0
38 minutes holding time The addition of sodium bicarbonate in Run 1 was seen to have a significant, favorable effect on the TCCA crystals while ammelide and ammonium bisulfate in Runs 4 and 6 had very unfavorable effects. These effects confirmed the importance of maintaining a mol ratio of at least 1, as in Run 1, rather than less than 1, as in Runs 4 and 6, where hypochlorous acid was consumed in chlorinating the amino group of ammelide or the ammonium group of ammonium bisulfate. The mol ratio was further reduced in Run 6 in that the alkalinity necessary to form hypochlorous acid was neutralized by the conversion of the bisulfate ion to sulfate.

EXPERIMENT 4

The procedure of Experiment 3 was repeated to show the effects from variations of the mol ratio on the yield, assay, and particle size and the results are reported in Table III. The data for Run 14, Table I, is included as a control. The control had a mol ratio of 1 and an initial feed pH of 6.6. All experimental conditions were the same as the control unless indicated otherwise.

Run 1

The mol ratio was adjusted to 0.95, using 1.15 g concentrated HCl per liter.

Run 2

The mol ratio was adjusted to 1.05 using 1.88 g 50% NaOH. The pH of the solution was immediately reduced from 8.0 to 7.0 by sparging with chlorine gas.

Run 3

The mol ratio was adjusted to 1.15 using 5.64 g 50% NaOH; the pH was reduced from 8.5 to 6.5 by sparging with chlorine.

Run 4

The control experiment was repeated with the addition of 0.5 g $NH_4HSO_4$. This decreased the mol ratio as caustic was consumed by the formation of chloramines and sulfate.

Run 5

Run 4 was repeated with the $NH_4HSO_4$ addition doubled to 1.0 g. While this increment had no further effect on the pH, it had a great adverse effect on the product quality.

Run 6

Run 5 was repeated with the addition of 6.6 g sodium bicarbonate which substantially improved the product quality.

Run 7

Run 5 was repeated with the addition of 2.3 g sodium carbonate which also substantially improved the product quality.

Run 8

The addition of 0.9 g ammelide to the control was observed to have a significant adverse effect.

Run 9

Run 8 was repeated with the addition of 2.0 g NaOH (3.55 mol per mol of ammelide) and with sparging of the solution with chlorine to maintain a pH of about 7.

Run 10

The solution was stored for 18 hours during which time the pH dropped from 6.6 to 5.02 and the available chlorine dropped from 36.35 g/l to 33.53 g/l. On chlorination, the product quality was poor.

Run 11

Run 10 was repeated. The available chlorine fell from 38.03 g/l to 34.40 g/l. The mol ratio was raised by adding 16 g of sodium bicarbonate which increased the pH from 4.91 to 6.37.

Run 12

Run 10 was repeated with the available chlorine falling from 38.03 g/l to 33.10 g/l. The addition of 5.6 g of sodium carbonate raised the pH from 4.91 to 7.95.

Run 13

After 42 hours storage the available chlorine dropped from 33.5 g/l to 31.0 g/l. The addition of 4.6 g of sodium carbonate increased the pH from 4.82 to 7.0.

Run 14

Run 13 was repeated. The available chlorine dropped from 34.24 g/l to 31.74 g/l. The addition of 5.8 g sodium carbonate increased the pH to 8.0 from 4.93.

Run 15

The control experiment was repeated with the solution stored 65 hours during which time the available chlorine dropped from 34.59 g/l to 29.07 g/l. The addition of 6.25 g of sodium carbonate to increase the mol ratio increased the pH from 5.0 to 7.0.

Run 16

Run 15 was repeated with the available chlorine dropping from 34.37 g/l to 30.07 g/l. The addition of 6.58 g of sodium carbonate increased the pH from 5.18 to 8.

In Runs 13 through 16 it was observed that although the yield dropped substantially, the product assay and crystal size were improved by adjusting the mol ratio to at least 1.0 with sodium carbonate.

The invention has been specifically described above in terms of sodium compounds as the alkali metal compounds taking part in or produced by the reactions. It is apparent that the corresponding potassium compounds can also be employed as the alkali metal compounds.

TABLE I

Effect of Sodium Chloride and Degree of Chlorination on TCCA Product Quality

| Run | g/l NaCl | Surf.* mg/l | Final pH | % Yield | % Assay | Crystal size μm |
|---|---|---|---|---|---|---|
| 1 | 0 | 0 | 3.0 | 84.9 | 98.9 | 40 × 15 |
| 2 | 0 | 50 | 3.5 | 85.8 | 99.1 | 45 × 20 |
| 3 | 0 | 50 | 3.0 | 87.2 | 99.6 | 60 × 22 |
| 4 | 0 | 50 | 2.5 | 89.9 | 99.8 | 50 × 30 |
| 5 | 75 | 50 | 3.0 | 83.5 | 92.4 | 70 × 15 |
| 6 | 100 | 50 | 3.0 | 83.5 | 98.6 | 90 × 10 |
| 7 | 125 | 50 | 3.0 | 82.5 | 86.6 | 200 × 10** |
| 8 | 90 | 50 | 3.0 | 81.1 | 99.2 | 60 × 12 |
| 9 | 90 | 50 | 3.0 | 86.9 | 98.5 | 60 × 20 |
| 10 | 90 | 50 | 3.2 | 85.3 | 98.5 | 55 × 7** |
| 11 | 90 | 50 | 3.4 | 84.4 | 97.9 | 70 × 8** |
| 12 | 90 | 50 | 3.6 | 82.6 | 98.0 | 75 × 15** |
| 13 | 90 | 50 | 3.8 | 81.7 | 98.0 | 70 × 8*** |
| 14 | 90 | 50 | 3.0 | 85.3 | 97.2 | 63 × 13*** |

*Surfactant - sodium dodecylbenzenesulfonate
**hazy filtrate indicating small crystals
***slight haze in filtrate indication of marginal quantity of small crystals

TABLE II
Effect of Additives on TCCA Product Quality

| Run | Variations mg/l | Addition | Filtrate Apprnce | Yield % | Assay % | Crystal μm |
|---|---|---|---|---|---|---|
| (Control Table I, Run 14) | | | haze*** | 85.3 | 97.2 | 63 × 13 |
| 1 | 1200 | NaHCO$_3$ | haze*** | 85.8 | 97.0 | 75 × 25 |
| 2 | 500 | Na$_2$SO$_3$ | clear | 85.3 | 98.8 | 70 × 12 |
| 3 | 140 | FeCl$_3$.6H$_2$O | milky | 86.3 | 97.2 | 80 × 8 |
| 4 | 225 | Ammelide | milky | 80.3 | 94.2 | 40 × 2 |
| 5 | 2500 | NaClO$_3$ | clear | 84.8 | 97.5 | 60 × 5 |
| 6 | 500 | NH$_4$HSO$_4$* | milky | 78.0 | 93.2 | Fines |
| 7 | 1250 | Na$_2$CO$_3$** | clear | 74.3 | 98.0 | 60 × 17 |
| Other Variations | | | | | | |
| 8 | Reaction Temp. 26° | | clear | 74.3 | 98.0 | 80 × 10 |
| 9 | Holding time 23.5 mins. | | hazy | 89.5 | 98.7 | 55 × 6 |

*feed pH 5.46
**feed pH 8.6, reaction pH 3.6
***slight haze observed

TABLE III
Effect of Mol Ratio on TCCA Product Quality

| Run No. | Variable | Remedy | Feed pH | Filtrate | Yield % | Assay % | Crystals μm |
|---|---|---|---|---|---|---|---|
| (Control Table I, Run 14) | | | 6.6 | haze** | 85.3 | 97.2 | 63 × 13 |
| 1 | mol ratio 0.95 | — | 4.72 | hazy | 79.8 | 96.7 | 60 × 5 |
| 2 | mol ratio 1.05 | — | 7.0* | clear | 83.0 | 98.1 | 60 × 5 |
| 3 | mol ratio 1.15 | — | 6.5* | clear | 82.6 | 98.6 | 70 × 10 |
| 4 | 0.5 g NH$_4$HSO$_4$ | — | 5.45 | hazy | 84.4 | 96.5 | 50 × 5 |
| 5 | 1.0 g NH$_4$HSO$_4$ | — | 5.46 | milky | 78.0 | 93.2 | Fines |
| 6 | 1.0 g NH$_4$HSO$_4$ | 6.6 g NaHCO$_3$ | 6.3 | haze** | 89.4 | 98.6 | 50 × 8 |
| 7 | 1.0 g NH$_4$HSO$_4$ | 2.3 g Na$_2$CO$_3$ | 6.2 | haze** | 85.8 | 98.0 | 80 × 7 |
| 8 | 0.9 g ammelide | — | 5.6 | milky | 80.3 | 94.2 | 40 × 2 |
| 9 | 0.9 g ammelide | 2.0 g NaOH | 7.0* | hazy | 89.0 | 97.6 | 50 × 5 |
| 10 | 18 hrs storage | — | 5.02 | milky | 75.7 | 96.1 | Fines |
| 11 | 18 hrs storage | 16 g NaHCO$_3$ | 6.37 | hazy | 86.3 | 98.5 | 60 × 15 |
| 12 | 18 hrs storage | 5.6 g Na$_2$CO$_3$ | 7.95 | clear | 85.3 | 99.4 | 60 × 17 |
| 13 | 42 hrs storage | 4.5 g Na$_2$CO$_3$ | 7.0 | haze** | 82.6 | 98.2 | 70 × 7 |
| 14 | 42 hrs storage | 5.8 g Na$_2$CO$_3$ | 8.0 | clear | 81.7 | 98.5 | 70 × 7 |
| 15 | 65 hrs storage | 6.25 g Na$_2$CO$_3$ | 7.0 | milky | 78.0 | 95.4 | 45 × 3 |
| 16 | 65 hrs storage | 6.58 g Na$_2$CO$_3$ | 8.0 | hazy | 78.9 | 97.6 | 65 × 5 |

*chlorine sparged in to adjust pH before feeding to crystallizer
**slight haze observed

I claim:

1. A process for producing both an alkali metal dichloroisocyanurate and trichloroisocyanuric acid by a two-stage chlorination comprising:
   (a) chlorinating an aqueous solution of a trialkali metal salt of cyanuric acid maintained at a temperature between 10° C. and 30° C. and at a pH between 5 and 9 thereby forming a slurry of alkali metal dichloroisocyanurate,
   (b) separating the undissolved alkali metal dichloroisocyanurate from the aqueous medium constituting the mother liquor,
   (c) whenever the mol ratio in the mother liquor of available alkalinity to chlorine required to convert any triazine compounds which are present to trichloroisocyanuric acid falls outside the range of 1.0 to 1.3, adding sufficient alkali metal salt of carbonic acid to the mother liquor to bring the mol ratio within the said range,
   (d) chlorinating the mother liquor from step (c) while maintaining the temperature between 10° C. and 30° C. and the pH between 2.5 and 3.5, and
   (e) recovering the resulting trichloroisocyanuric acid so produced.

2. The process of claim 1 wherein the alkali metal dichloroisocyanurate is sodium dichloroisocyanurate.

3. The process of claim 1 wherein the first chlorinator pH is maintained at 6.5 to 7.5.

4. The process of claim 1 wherein the mol ratio of the mother liquor in step (c) is adjusted to be within the range of 1.0 to 1.15.

5. The process of claim 1 wherein the temperature of the second chlorinator is maintained between 10° C. to 20° C.

6. The process of claim 1 wherein the pH of the second chlorinator is maintained between 3.3 and 3.0.

7. The process of claim 1, 2, 3, 4, 5, or 6 wherein the mol ratio of the mother liquor is adjusted to be within the range of 1.0 to 1.15.

8. The process of claim 7 wherein the temperature of the second chlorinator is maintained between 10° C. and 20° C.

9. The process of claim 8 wherein the pH of the second chlorinator is maintained between 3.3 and 3.0.

10. The process of claim 7 wherein the alkali metal salt of carbonic acid comprises sodium bicarbonate.

11. The process of claim 7 wherein the alkali metal salt carbonic acid comprises sodium carbonate.

12. The process of claim 7 wherein the alkali metal salt of carbonic acid comprises sodium carbonate sesquicarbonate.

13. The process of claim 7 wherein the alkali metal salt comprises potassium bicarbonate.

14. The process of claim 7 wherein the alkali metal salt of carbonic acid comprises potassium carbonate.

15. An improved two-stage chlorination process for making trichloroisocyanuric acid by chlorinating an aqueous slurry of a trialkali metal cyanurate in a first chlorinator maintained at a pH between 6.5 and 8.5, withdrawing an effluent from the first chlorinator and feeding it to a second chlorinator maintained at a pH between 2.5 to 3.5 and withdrawing an effluent from the second chlorinator and recovering trichloroisocyanuric acid from the effluent of the second chlorinator wherein the improvement comprises:
   (a) monitoring the mol ratio of available alkalinity to chlorine required to convert any triazine compounds which are present to trichloroisocyanuric acid in the effluent from the first chlorinator,
   (b) whenever the mol ratio of the effluent from the first chlorinator falls outside the range of 1.0 to 1.3, adjusting said mol ratio of the effluent of the first chlorinator to be within 1.0 to 1.3 by adding an alkali metal salt of carbonic acid,
   (c) continuously adding the monitored and adjusted effluent to the second chlorinator.

* * * * *